(12) United States Patent
Benning et al.

(10) Patent No.: US 7,687,944 B2
(45) Date of Patent: Mar. 30, 2010

(54) ACTUATION SYSTEM FOR PERSONAL CARE APPLIANCE USING LINEAR ACTUATORS

(75) Inventors: Wolter Benning, Seattle, WA (US); John W. Pace, Bothell, WA (US)

(73) Assignee: Koninklijke Philips Electronics N.V., Eindhoven (NL)

(\*) Notice: Subject to any disclaimer, the term of this patent is extended or adjusted under 35 U.S.C. 154(b) by 70 days.

(21) Appl. No.: 12/066,373

(22) PCT Filed: Sep. 8, 2006

(86) PCT No.: PCT/IB2006/053165

§ 371 (c)(1),
(2), (4) Date: Mar. 10, 2008

(87) PCT Pub. No.: WO2007/029201

PCT Pub. Date: Mar. 15, 2007

(65) Prior Publication Data

US 2008/0254407 A1 Oct. 16, 2008

Related U.S. Application Data

(60) Provisional application No. 60/715,227, filed on Sep. 8, 2005.

(51) Int. Cl.
*A61C 17/16* (2006.01)
*A61C 17/34* (2006.01)
*H02K 33/04* (2006.01)
*H02K 33/00* (2006.01)

(52) U.S. Cl. .............. 310/15; 310/20; 310/36; 310/12.01; 15/22.1; 15/22.2; 15/26

(58) Field of Classification Search ............. 310/12–14, 310/20, 36, 21, 22, 33, 34, 37, 47, 50; 15/22.1, 15/22.2, 26
See application file for complete search history.

(56) References Cited

U.S. PATENT DOCUMENTS

| 5,585,686 | A | * | 12/1996 | Kataoka ............... 310/341 |
| 5,678,312 | A | | 10/1997 | Watanabe |
| 5,921,134 | A | * | 7/1999 | Shiba et al. ............ 74/110 |
| 6,098,288 | A | * | 8/2000 | Miyagawa et al. ...... 30/43.91 |
| 6,821,119 | B2 | | 11/2004 | Shortt |
| 7,443,058 | B2 | * | 10/2008 | Shimizu et al. ........ 310/12.04 |
| 2004/0010871 | A1 | | 1/2004 | Nishinaka et al. |
| 2006/0071561 | A1 | * | 4/2006 | Chiu et al. ............. 310/20 |

FOREIGN PATENT DOCUMENTS

| EP | 1376833 | | 1/2004 |
| JP | 06245820 | | 2/1993 |
| JP | 09252843 | A * | 9/1997 |
| WO | 9815235 | | 4/1998 |
| WO | 2004047670 | | 6/2004 |

\* cited by examiner

*Primary Examiner*—Quyen Leung
*Assistant Examiner*—Leda Pham

(57) ABSTRACT

The personal care appliance drive system includes a pair of linear actuators capable of operating both in an opposing phase mode or in a parallel (in-phase) mode. The system includes a motion converter assembly which converts the opposing phase action of the two linear actuators into a rotational action of an output drive shaft and converts in-phase action to a translation motion of the output shaft or to drive another function of the appliance, such as a pump. The motion converter, operating simultaneously in an opposing phase mode and in-phase modes, produces a complex motion of the workpiece.

10 Claims, 3 Drawing Sheets

ACTUATION SYSTEM FOR PERSONAL CARE APPLIANCE USING LINEAR ACTUATORS

This invention relates generally to an actuation system for a personal care appliance, such as a power toothbrush, and more specifically concerns an actuation system using two linear actuators and a motion converter to produce a resulting desired action of a workpiece mounted on a drive shaft portion of the appliance.

Many different actuation/drive systems for power toothbrushes are known, including various mechanical, electromechanical and magnetic arrangements. A significant problem with many such drive systems is the resulting vibration of the handle and noise caused by the action of the drive system. Various forms of damping have been used to reduce this undesirable noise and/or handle vibration. Also, various spring/motor arrangements have been designed to attempt to cancel the vibration in the handle. Many of these vibration-canceling/damping systems, however, are complicated and expensive; others do not accomplish the desired result.

Hence, it is desirable to have a drive system in which vibration is canceled or minimized by virtue of the design of the drive system itself.

Accordingly, the present invention is a drive system for a personal care appliance, comprising: first and second linear actuators, capable of operating in opposing phase or in-phase modes; and a motion converter for converting the opposing phase mode into a rotational action of an output drive shaft and a workpiece mounted thereon, and converting the in-phase mode into a translational action of the output drive shaft or another element to accomplish a selected function.

Figure 1:
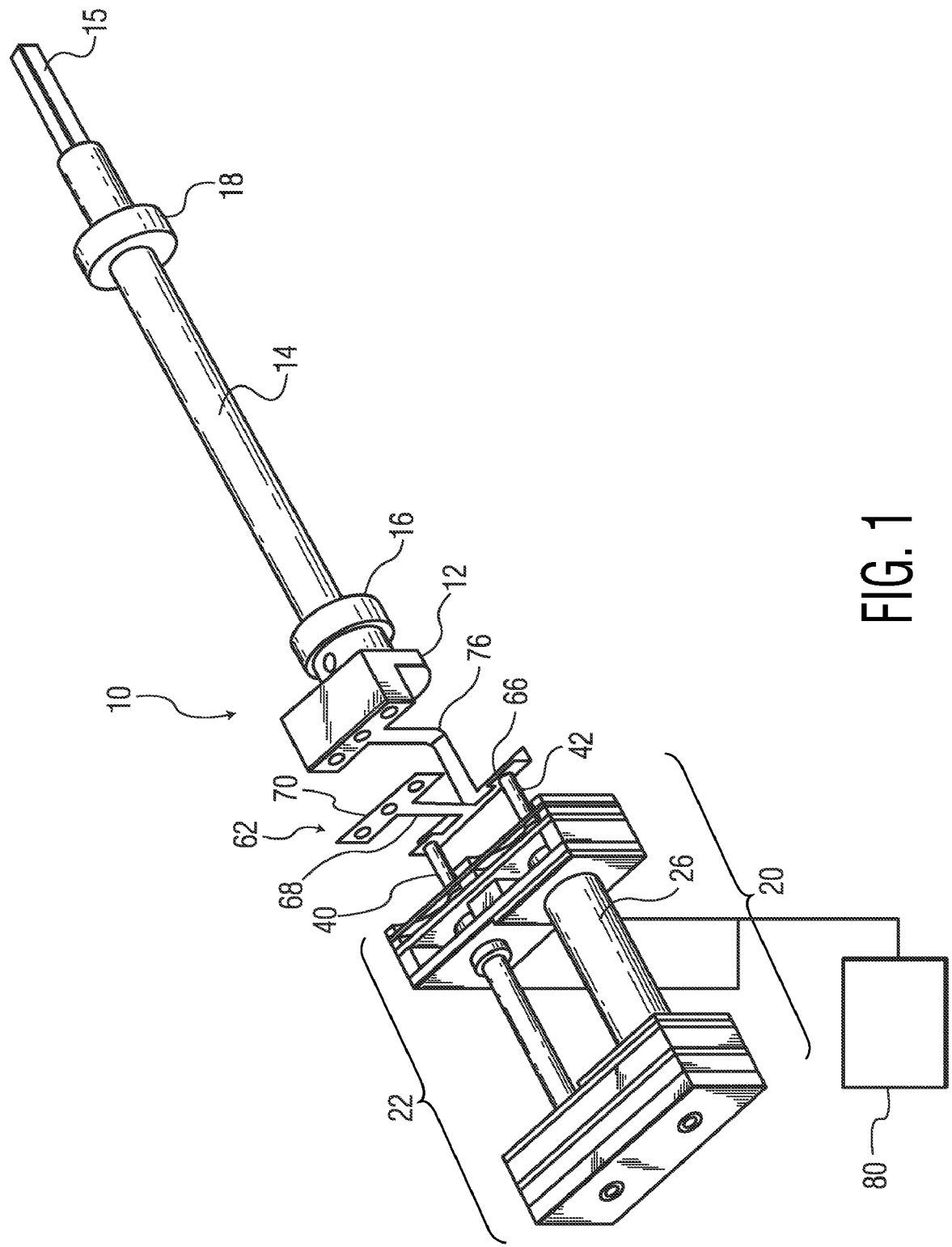
FIG. 1 is a perspective view showing the overall actuation system of the present invention.

FIG. 1 shows an embodiment of the drive/actuation system of the present invention. It is referred to generally at 10 and is shown driving an output shaft attachment member 12, to which an output drive shaft 14 is secured. In FIG. 1, output shaft 14 is shown supported by two spaced rotary and linear bearings 16 and 18, although these are not necessary to the appliance system. At the free end 15 of output shaft 14 is mounted a workpiece (not shown) which could for example be a toothbrush brushhead or other personal care appliance member. The terms "drive assembly" and "actuation assembly" are used interchangeably herein and are used to refer to system 10. The apparatus shown and described may be used for personal care appliances, such as electric toothbrushes and other small appliances with reciprocating and/or oscillating motion.

Figure 2:
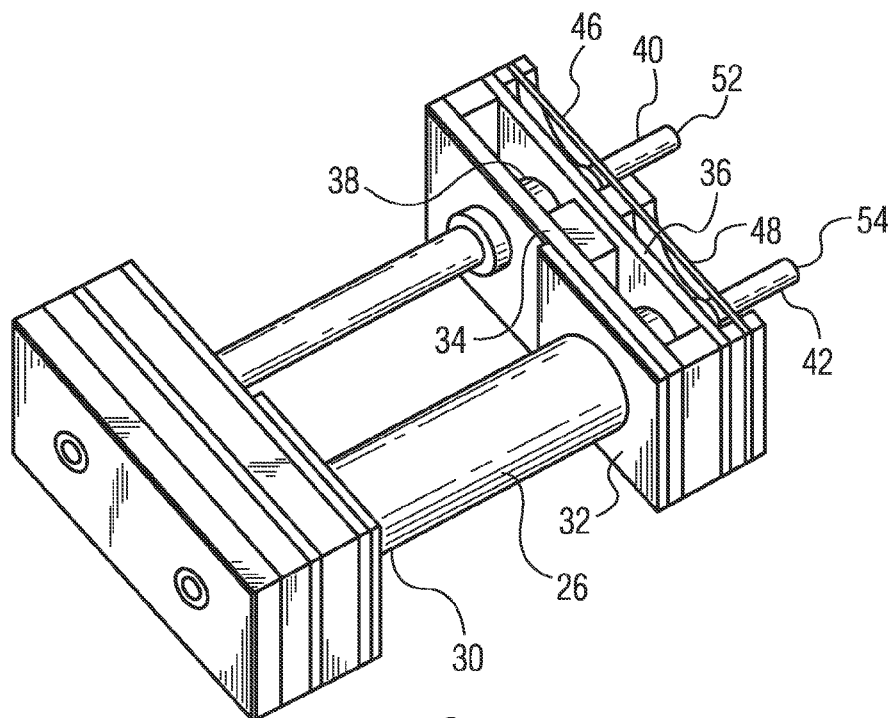
FIG. 2 is a perspective view showing the dual linear actuator portion of the actuation system of FIG. 1.

Drive system 10 includes two linear actuators 20 and 22. Any pair of linear actuators can be used. A magnetic embodiment with two linear actuators is shown in FIGS. 1 and 2. The magnetic system includes two central parallel coils (only one coil 26 is shown) with magnet assemblies positioned at the opposing ends 30 and 32 of the coils. Each magnet assembly includes two steel plates 34 and 36 and a center magnet 38. The magnets in each magnet assembly are oriented in opposing polarity. The magnet assemblies, respectively, include armatures 40 and 42, each armature being supported in parallel by two suspension/return leaf springs 46 and 48. The armatures 40 and 42 move back and forth as an alternating electric current is applied to the actuating coils. End portions 52 and 54 of the two armatures 40 and 42, respectively, extend outwardly from the suspension springs as shown for use in the appliance drive system 10. As indicated above, various types of linear actuators can be used in the drive system shown and described herein. The magnetic arrangement of FIG. 2 is one example. Other possibilities include a flat linear drive system, a variable air gap drive system, and a hydraulic system. The motion converter portion of the present system translates the dual linear motion into a rotation and/or translation of the output shaft, as described below.

The free ends of the two end portions 52 and 54 of armatures 40 and 42 are secured to the rear end of yoke portion 62 of a motion converter assembly 64. In the embodiment shown, yoke portion 62 is a sheet metal member having a horizontal base element 66, a vertical element 68 which extends upwardly from the middle of the base element 66, and a horizontal attachment member 70 at the upper end of the vertical element 68. Attachment member 70 has a plurality of openings 72-72 therein, which permit convenient attachment of the yoke portion 62 to a housing of the appliance by means of screws, etc. The yoke portion 62 is typically made from sheet metal and is approximately 0.008 inch thick.

The free ends of the end portions 52 and 54 of the two armatures are secured to the opposing ends 67, 69 of base element 66 of yoke portion 62. In operation, when the two actuators are driven in opposite phase, such that as one actuator moves out, the other actuator moves in and vice versa, one end 67 of the yoke base element 66 moves inwardly, toward the magnetic actuator, while the other end 69 moves away from the actuator and vice versa. In this arrangement, the mid-point of base element 66 from which vertical element 68 extends is a stationary point. Element 68 twists along its length as the ends 67, 69 of base element 66 move oppositely toward and away from the actuator. The dynamic reaction forces of the two armatures 40 and 42 on the leaf springs 46 and 48 oppose each other and cancel each other out. This results in a significant reduction in vibration transferred to the appliance housing.

Figure 3:
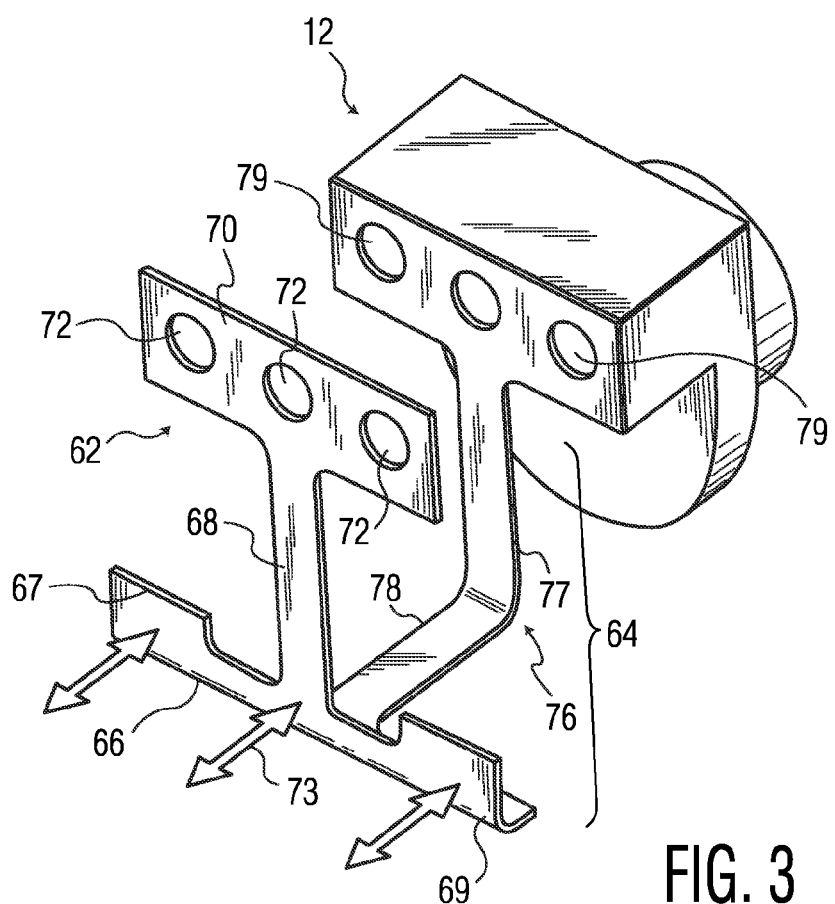
FIG. 3 is a perspective view showing the yoke and motion converter portions of the actuation system of FIG. 1.

Also shown in FIG. 3 in detail is an L-converter portion 76 of the motion converter assembly 64. The L-converter portion 76 is an L-shaped portion of sheet metal, which extends horizontally from the base element 66 of yoke portion 62, approximately at its mid-point. The vertical leg 77 extends to an output shaft attachment mechanism 12. In the embodiment shown, L-converter 76 is approximately 0.08 inch wide and 0.008 inch thick, with the horizontal and vertical legs 78, 77 each approximately 0.4 inch long. The included angle between the two legs can vary between 70-110° without compromising the function of the L-converter. In one arrangement of the present embodiment, base element 66, yoke portion 62 and L-converter 76 are formed from a single piece of light steel sheet metal. As indicated above, vertical leg 77 of L-converter 76 is attached to output shaft attachment member 12. The output shaft attachment member 12 is a steel block which is attached by means of screws or the like through openings 74 in member 12 to the housing of the appliance.

Extending from attachment member 12 is the output drive shaft 14 (FIG. 1), which moves in response to the action of linear actuators. As indicated above, base member 66 of yoke portion 62 will twist (rotate) about its mid-point. This action is transmitted by the L-converter 76 to the output shaft attachment member 12, resulting in a rotation of the output shaft 14 about its longitudinal axis. The amount of rotation of the shaft will depend upon the amount of deflection of the base element 66 produced by action of the two linear actuators. The frequency of operation can be selected by the operator by a frequency control unit 80, or the frequency can be established by the manufacturer.

In the other mode of movement, the actuators, specifically armatures 40 and 42, operate in parallel with each other, i.e. they go back and forth together, produced by two drive signals which are in phase with each other. This produces a back-and-forth action of the entire base element 66 and a push/pull action on the L-converter 76. This action can be used to produce a translation, i.e. back-and-forth action, of the attachment member 12 and the output drive shaft 14, or it can be used to drive an additional function in the appliance, such as a dentifrice pump in a power toothbrush. This action is shown by the double arrow 73 in FIG. 3. When the other mode of movement is used to provide an additional function, such as a pumping action, there is no translational motion of the output drive shaft and the workpiece. The frequency of this mode of operation can also be selected by the operator with frequency control unit 80, or it can be set by the manufacturer.

In another arrangement, two different sets of drive signals can be simultaneously applied to the magnetic actuators, resulting in both a twisting (rotational) action of the yoke from one set of drive signals and a translational action of the yoke from another set of drive signals. One set of drive signals will be out-of-phase, while the other set of drive signals can be in-phase. For instance, the out-of-phase set of drive signals can be relatively high frequency, e.g. 260 Hz, while the in-phase drive signals could be a significantly lower frequency, e.g. 80 Hz. This results in a complex motion of the workpiece, when both drive signals are applied to the same output shaft. The frequencies of the two drive signals can be selected by the operator, i.e. they are programmable, by means of control unit 80, so that different complex actions of the workpiece can be conveniently obtained, simply by changing the respective frequencies of the two drive signals, or by using a selected single frequency for a single mode of operation.

Figure 4A:
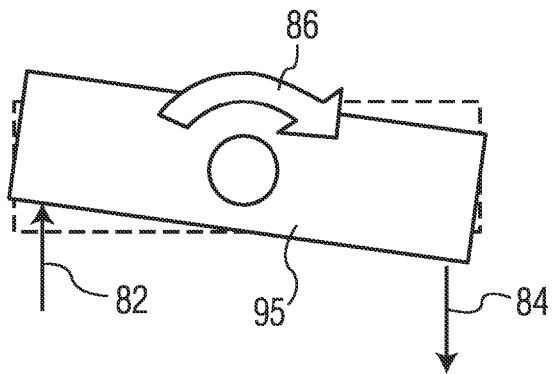
FIGS. 4A, 4B and 4C show different modes of possible notion of the appliance workpiece with the actuation system of FIG. 1.
Figure 4B:
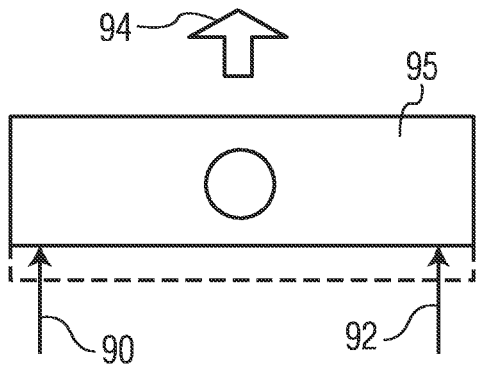
Figure 4C:
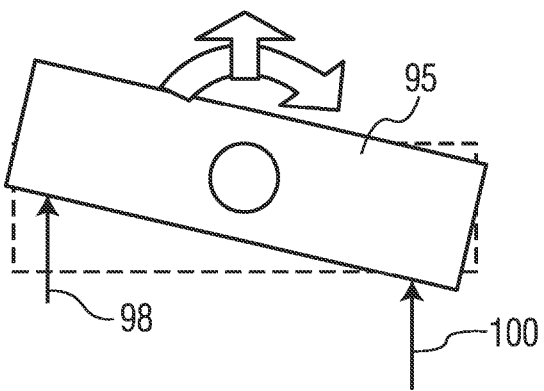

FIGS. 4A, 4B and 4C show three possible actions of the yoke portion 62 produced by the linear actuators. In FIG. 4A, an opposing phase drive (produced by opposing phase drive signals) creates a rotation of yoke portion 62 about its vertical element portion 68. The yoke portion is represented by block member 95. Opposing action of the two actuators on base element 66 is shown by the opposing arrows 82, 84, with the resulting rotational action shown by the curved arrow 86.

FIG. 4B shows the action of the linear, translational motion mode of the system, where the actuators are operating in parallel, produced by drive signals which are in phase. The parallel, action of the actuators on base element 66 is shown by the two arrows 90 and 92, resulting in a translation of the center vertical element 68 of the yoke, as shown by arrows 94.

FIG. 4C shows the superposition of the two drive actions, in which one set of drive signals produces a rotational action, while the other set of drive signals produces a translational action. The center of the yoke will receive only the translational action. At one end of member 66, the rotational action will add to the translational action (arrow 98), while at the other end, the rotational action will subtract from the translational action (arrow 100). The action will reverse in the next half cycle of the drive signals.

The personal care appliance could be a power toothbrush. In operation, the rotational action of the brushhead in one arrangement could be approximately 20°, with a translational action within the range of 0-0.2 inch. Other actions can be conveniently obtained, depending on the drive frequency and arrangement.

Accordingly, a drive system/actuator for a personal care appliance using two linear actuators and a motion converter has been shown and described. The motion converter in this case includes a yoke portion and an L-converter portion, which is in turn secured to an output shaft attachment member. The actuators can be driven in a parallel mode and an opposing phase mode, which can produce various actions of the output shaft, or an action of the output shaft and another function of the appliance.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. A drive system for a personal care appliance, comprising: first and second linear actuators, capable of operating in opposing phase or in phase modes; and a motion converter for converting the opposing phase mode action into a rotational action of an output drive shaft and a workpiece mounted thereon, and converting the in phase mode action into a translational action of the output drive shaft or other element to accomplish a selected function, wherein the motion converter includes a flexible yoke portion which in turn includes an elongated base member, wherein the first and second linear actuators are secured to opposing ends of the base member, the yoke portion further including a vertical member which extends upwardly from the base member at approximately a mid-point thereof and wherein the yoke portion is adapted for attachment to the housing of the personal care appliance at an upper end of the vertical member.

2. The drive system of claim 1, including a frequency control system for the linear actuators, controllable by an operator, to select a frequency for the opposing phase and/or the in phase modes of operation of the device.

3. The drive system of claim 2, wherein the frequency control system (80) is programmable.

4. The drive system of claim 1, wherein the motion converter further includes an L converter, which comprises a flexible L shaped section of material which extends from approximately the mid-point of the base member of the yoke portion, to an output shaft attachment assembly, the output shaft attachment assembly adapted being to be secured to the housing of the personal care appliance, and wherein an output shaft on which the workpiece is mounted extends from the attachment assembly.

5. The drive system of claim 4, wherein the yoke portion and the L converter portion are made of sheet metal.

6. The drive system of claim 2, wherein the frequency of operation for the opposing phase mode is approximately 260 Hz, and wherein the frequency of operation in parallel phase mode is approximately 80 Hz.

7. A drive system for a personal care appliance, comprising: first and second linear actuators, capable of operating in opposing phase or in phase modes; and a motion converter for converting the opposing phase mode action into a rotational action of an output drive shaft and a workpiece mounted thereon, and converting the in phase mode action into a translational action of the output drive shaft or other element to accomplish a selected function, wherein the personal care appliance is a power toothbrush and includes a brushhead member secured to the free end of the output shaft, and wherein the motion converter is configured so as to produce a rotation of the workpiece within the range of 0-20° in response to the action of the first and second linear actuators.

8. The drive system of claim 4, wherein the yoke portion and the L converter portion are made from a single piece of material.

9. The drive system of claim 1, wherein the personal care appliance is a power toothbrush and includes a brushhead member which is secured to a free end of the output shaft (14), and wherein the motion converter is configured and arranged so as to produce a translation of the workpiece within the range of 0-0.2 inch in response to action of the first and second linear actuators.

10. A drive system for a personal care appliance, comprising: first and second linear actuators, capable of operating in an opposing phase mode; and a motion converter for converting the opposing phase mode action into a rotational action of an output drive shaft and a workpiece mounted thereon, to accomplish a selected function, wherein the motion converter includes a flexible L shaped section of material to which the first and second linear actuators are secured, to produce a rotational action of the output shaft.

* * * * *